United States Patent [19]

Porter

[11] Patent Number: 5,766,197
[45] Date of Patent: Jun. 16, 1998

[54] SURGICAL CUTTING INSTRUMENT WITH ANTI-TORGUE OUTER JACKET

[75] Inventor: Ronald V. Porter, Meredith, N.H.

[73] Assignee: Portlyn Corporation, Moultonboro, N.H.

[21] Appl. No.: 752,430

[22] Filed: Nov. 19, 1996

Related U.S. Application Data

[63] Continuation of Ser. No. 422,049, Apr. 14, 1995, abandoned.

[51] Int. Cl.$^6$ ............................................. A61B 10/00
[52] U.S. Cl. ........................ 606/170; 128/749; 606/205
[58] Field of Search ............................... 606/170, 205, 606/206, 207, 208; 128/751, 749, 759

[56] References Cited

U.S. PATENT DOCUMENTS

| | | | |
|---|---|---|---|
| 4,982,727 | 1/1991 | Sato | 606/205 X |
| 5,035,248 | 7/1991 | Zinnecker | 606/205 X |
| 5,061,238 | 10/1991 | Shuler . | |
| 5,137,013 | 8/1992 | Chiba et al. | 606/205 |
| 5,250,073 | 10/1993 | Cottone, Jr. . | |
| 5,320,635 | 6/1994 | Smith . | |
| 5,322,505 | 6/1994 | Krause et al. . | |

OTHER PUBLICATIONS

"DynaBite, Biopsy Forceps", Portlyn Medical Products; Copyright 1993.
"A Total Manufacturing Capability Dedicated To Medical Products And Components" Portlyn Medical Products; Copyright 1993.

*Primary Examiner*—Michael Buiz
*Assistant Examiner*—Patrick W. Rasche
*Attorney, Agent, or Firm*—Hayes, Soloway, Hennessey, Grossman & Hage, P.C.

[57] ABSTRACT

A surgical cutting instrument comprising an elongated flexible hollow-body tube having a lumen extending therethrough, and having a proximal end and distal end, together with an outer jacket, a forceps cutter for cutting coupled to the distal end of said body portion. A control wire having proximal and distal ends extends through the lumen in the body portion and is coupled at the distal end to the forceps cutter. A portion of the outer jacked comprises a right-hand wrap, while another portion comprises a left-hand wrap whereby to reduce torque displacement at the distal end upon cutting.

10 Claims, 2 Drawing Sheets

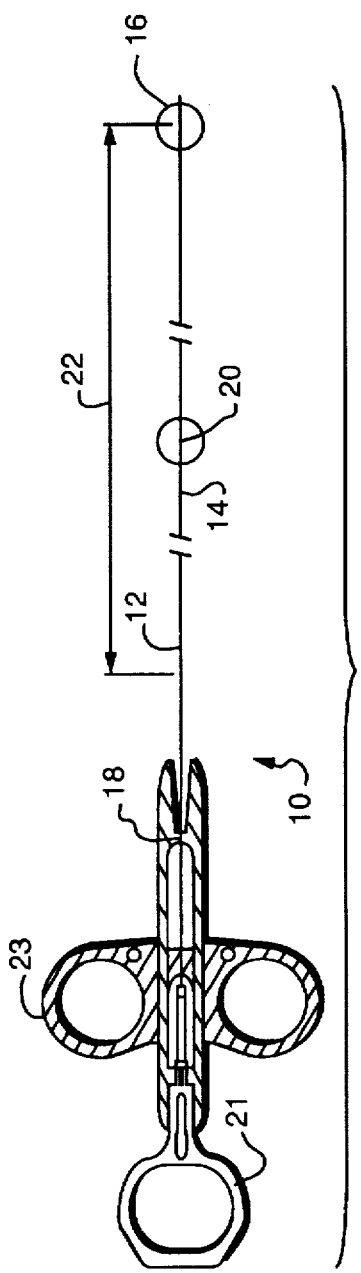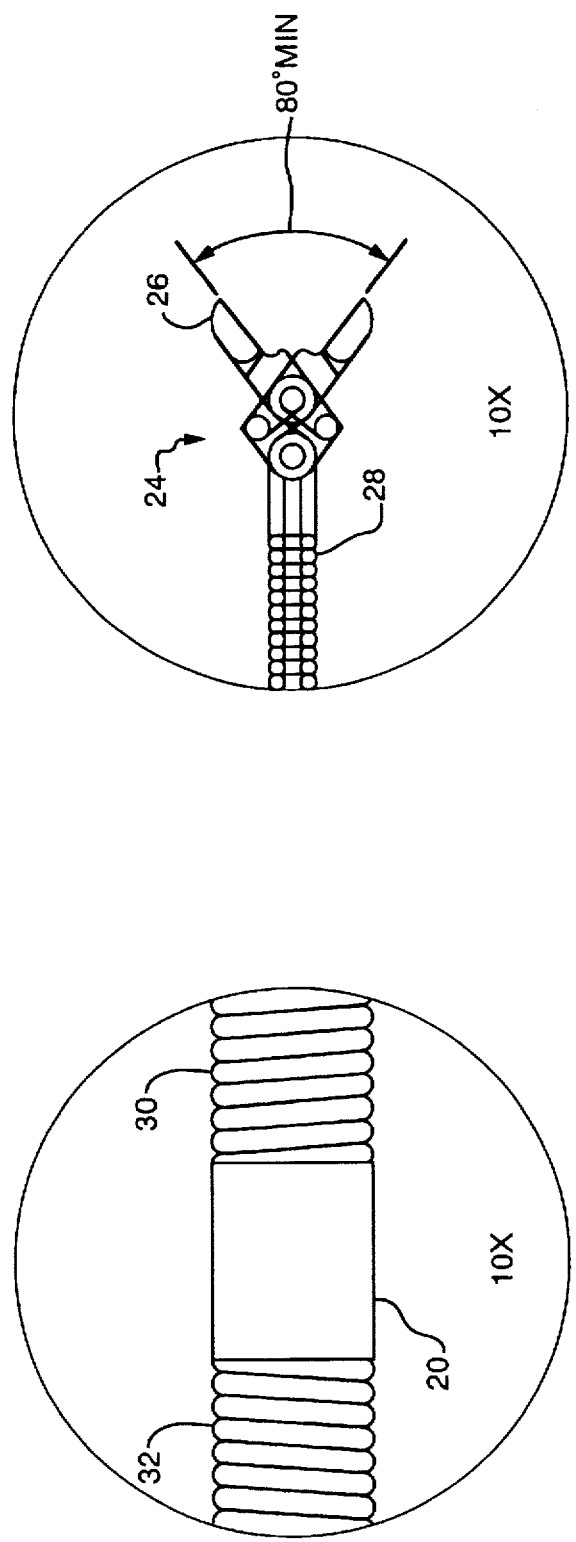

SURGICAL CUTTING INSTRUMENT WITH ANTI-TORGUE OUTER JACKET

This is a continuation of application Ser. No. 08/422,049 filed on Apr. 14, 1995 now abandoned.

BACKGROUND OF THE INVENTION

1. Field of the Invention

The present invention pertains to surgical cutting instruments, and, more particularly, to surgical cutting instruments having elongated inner and outer tubular members with distal ends cooperating to cut or resect bodily tissue, characterized in that the outer jacket contains means for reducing torque distortion without sacrifice in cutting force.

2. Background

The use of elongated surgical cutting instruments has become well accepted in performing closed surgery, such as orthoscopic or, more generally, endoscopic surgery. As described in U.S. Pat. No. 5,061,238, in closed surgery, access to the surgical site is gained via one or more portals, and instruments used in the surgical procedure must be elongated to permit the distal ends of the instruments to reach a desired location in a patient. Surgical cutting instruments for use in closed surgery conventionally have an elongated outer tubular member terminating at a distal end having an opening in a side wall, the end wall, or both, to form a cutting port or window end and an elongated inner tubular member concentrically disposed in the outer tubular member and having a distal end disposed adjacent the opening in the distal end of the outer tubular member. The distal end of the inner tubular member has a surface or edge for engaging tissue via the opening in the distal end of the outer tubular member and in many cases cooperates with the opening to shear and cut tissue. The '238 patent goes on to disclose an elongated bearing structure for a surgical cutting instrument having elongated inner and outer tubular members which are said to prevent cocking or skewing of the inner member relative to the outer member without creating galling and possible seizure during operation of the surgical cutting instrument.

In U.S. Pat. No. 5,250,073, there is described a torqueable and formable biopsy forceps. The biopsy forceps are said to provide improved torqueable and formable characteristics. The device includes a handle and core wire connected at its proximal end to the handle and connected at its distal end to a forceps assembly. The control wire displacing device carried by the handle serves to displace the core wire for moving the core wire between a forceps open position and a forceps closed position. The core wire includes at least three elongated portions, including a proximal portion having a proximal end secured to the wire displacing means, a distal portion having a distal end secured to the forceps assembly and an intermediate portion located between the proximal and distal portions. The proximal portion is said to be of greater length than the intermediate or distal portions and of greater diameter than the intermediate portion which, in turn, is said to be of greater diameter than the distal portion.

In U.S. Pat. No. 5,324,301, there is described a surgical instrument Comprising inner and outer tubular members with a coating of tin-nickel alloy on the outer surface of the inner tubular member and/or the inner surface of the outer tubular member to provide an elongated bearing surface between the tubular members.

In U.S. Pat. No. 5,322,505, there is described a surgical instrument that includes a rigid outer member within which is disposed a hollow inner member having rigid proximal and distal ends ahd a region disposed between the rigid proximal and distal ends that is relieved to render such region flexible.

With regards to the above, although various prior art devices have been manufactured, as noted, to improve the performance of surgical instruments for closed surgery procedures, one long-standing problem has emerged which is the tendency of such surgical cutting instruments to rotate in the direction corresponding to the wire wrapping on the surface of the outer jacket. That is, the surgical cutting instruments of the prior art generally have disposed on the outer jacket a wire-wrap with a constant and continuous right or left-hand wrap configuration. As a consequence, upon activation of the control wire displacement means which runs through the inner regions of the outer tubular member, the surgical cutting instrument tends to rotate or torque in the direction of the wrap. Moreover, there is a measured reduction in the force transmitted to the distal end cutting jaws.

Accordingly, it is a primary objection of the present invention to overcome the various problems and disadvantages associated with surgical cutting instruments of the prior art both which tend to displace from a target location, and sacrifice cutting strength, in a closed surgical procedure.

Another object of the present invention is to provide a surgical cutting instrument which contains an anti-torque outer jacket, which eliminates torque distortion and reduces the loss in force delivered to the distal cutting means, A more specific object of the present invention is to provide a surgical cutting instrument formed from an elongated flexible hollow-body tube having a lumen extending therethrough, and having a proximal end and distal end together with an anti-torque outer jacket.

SUMMARY OF THE INVENTION

The present invention provides a surgical cutting instrument comprising an elongated flexible hollow-body tube having a lumen extending therethrough, and having a proximal end and distal end, together with an anti-torque outer jacket, a means for cutting coupled to the distal end of said body portion, a control wire means having proximal and distal ends extending, through the lumen in said body portion and coupled at said distal end to said cutting means, characterized in that the anti-torque outer jacket operates to reduce torque displacement at the distal end upon cutting.

BRIEF DESCRIPTION OF THE DRAWINGS

Further objects and advantages of the present invention will become clear from the following detailed description taken with the accompanying drawings, wherein like numbers depict like parts and wherein:

FIG. 1 is a side elevation of one embodiment of surgical cutting instrument according to the present invention;

FIG. 1A is an enlarged side elevation, partially broken away, of the distal end of the surgical cutting instrument of FIG. 1;

FIG. 1B is an enlarged side view of the anti-torque outer jacket, showing in more detail the outer wire wrapping.

DESCRIPTION OF THE PREFERRED EMBODIMENT

Figure 2:
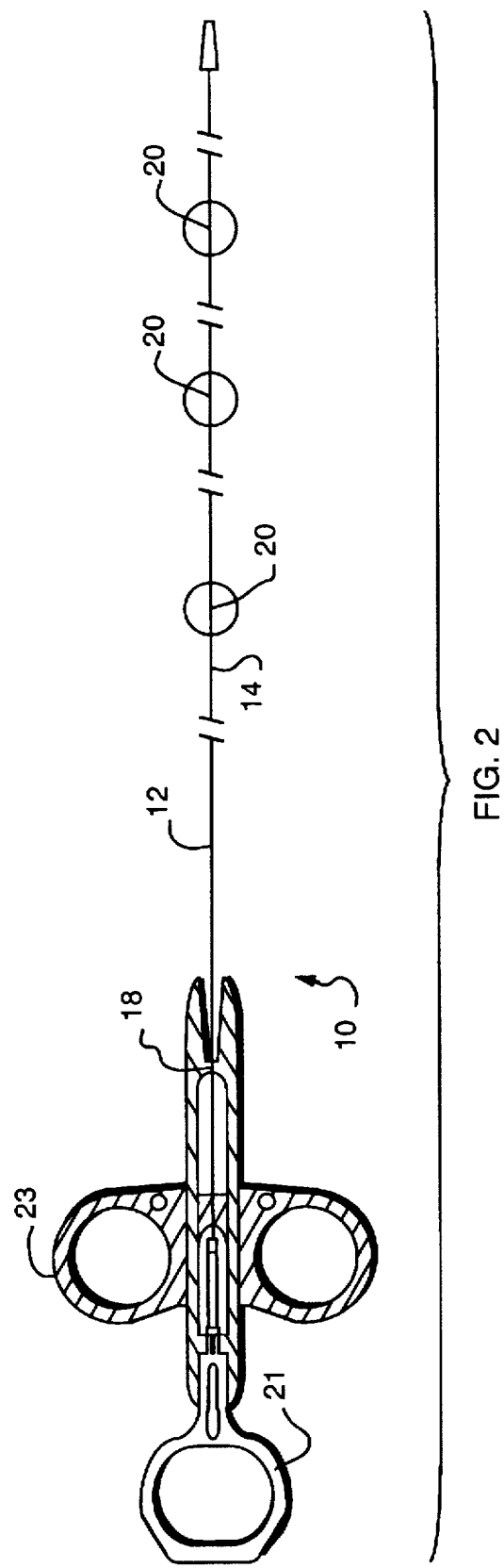
FIG. 2 is a view similar to FIG. 1 of another embodiment of surgical cutting instrument according to the present invention.

With reference to FIG. 1 a surgical cutting instrument 10 is shown comprising an elongated, flexible, hollow-body tube 12 having a lumen extending therethrough, and having a proximal end and distal end, together with an anti-torque outer jacket 14, a means for Cutting coupled to the distal end of said body portion 16, a control wire means 18 having proximal and distal ends extending through the lumen in said body portion and coupled at said distal end to said cutting means, characterized in that the anti-torque outer jacket operates to reduce torque displacement at the distal end upon cutting.

The anti-torque outer jacket preferably comprises wire surrounding said elongated, flexible, hollow-body tube, wherein a portion of the wire comprises a right-hand wrap 30, and another portion comprises a left-hand wrap 32. With reference to FIGS. 1A and 1B, the two regions of dissimilar wire wrapping are preferentially bridged by the use of a braze joint or laser weld 20 located along the length of the elongated, flexible, hollow-body tube. As shown at 22, the elongated, flexible, hollow-body tube can be about 20–300 cm in length, and at such length, the anti-torque outer jacket operates efficiently to reduce the previously described torque displacement. The significance of this feature is underscored by the fact that many of the prior art devices were limited in length, and limited for a given closed surgical procedure, due to their tendency to torque and concommitant lowered cutting strength, at lengths in excess of about 130 cm.

As also illustrated in FIG. 1A, the surgical cutting instrument contains means for cutting which preferably comprises a forceps assembly, including a pair of forceps. This is shown more specifically in FIG. 1A, which represents a magnified view of the distal end of the surgical cutting instrument of FIG. 1. With reference to FIG. 1A, the forceps assembly is shown generally at 24 with the forceps appearing at 26. It can be appreciated that the forceps assembly is preferably brazed, threaded or laser welded to the hollow-body tube at 28 and the forceps assembly is connected to a control wire displacement means which displaces said control wire for moving the cutting means between an open and closed position.

In a particularly preferred embodiment, and with reference to FIG. 1B, the anti-torque outer jacket comprises, along one-half of its length, a round wire right-hand wrap segment 30 and for the other half of its length, a round wire with a left-hand wrap segment 32. The balance of this alternating block concentric configuration on the elongated flexible hollow tube, as previously noted, serves to reduce the torque experienced at the distal end when the control wire displacement means is activated, by the operation of 21 as shown in FIG. 1. That is, by insertion of the fore finger and middle finger in the holding device 23 and the drawing together of 21 and 23, the elongated, flexible, hollow-body tube containing the anti-torque outer jacket is made to move relative to the control wire 18 thereby forcing the forceps assembly to essentially withdraw into the hollow-body tube and force the cutting means 26 into a closed position. However, to the extent that such an application of tensile force tends to torque the cutting means in one or another direction, such tendency is substantially neutralized by the outer alternating wire-wrapping configuration surrounding the outer jacket.

The present invention is subject to modification. For example, as shown in FIG. 2, the outer jacket may comprise two or more right-hand wrap segments 30 alternating with a like number of left-hand wrap segments 32. Such multiple segmented jackets are particularly useful in the case of the longer length instruments. Still other variations, modifications and changes in detail may be made without departing from the spirit and scope of the invention. It is therefore intended that the subject matter discussed above, and shown in the accompanying drawings be interpreted as being illustrative and not in a limiting sense.

I claim:

1. A surgical cutting instrument comprising:

an elongated flexible hollow-body tube having a lumen extending therethrough, and having a proximal end and distal end together with an anti-torque outer jacket;

a forceps cutter for cutting coupled to the distal end of said hollow-body tube;

a control wire having proximal and distal ends, extending through the lumen and coupled at its distal end to said forceps cutter;

characterized in that the anti-torque outer jacket reduces torque displacement at the distal end upon cutting wherein the anti-torque outer jacket comprises wound wire surrounding said elongated flexible hollow body tube, wherein a portion of the wire comprises a right hand wrap, and a corresponding portion comprises a left-hand wrap, and said portions are affixed to one another and said portions have substantially the same lengths.

2. The surgical cutting instrument of claim 1, wherein the right hand wrap and left-hand wrap portions are affixed to one another through a braze joint.

3. The surgical cutting instrument of claim 1, wherein the anti-torque outer jacket comprising wire includes at least two right-hand wrap segments alternating with an even number of left-hand wrap segments.

4. The surgical cutting instrument of claim 1, wherein the elongated flexible hollow body tube is about 20–300 cm in length.

5. The surgical cutting instrument of claim 1, wherein the elongated flexible hollow body tube has a diameter of about 0.5 mm to 3.5 mm.

6. The surgical cutting instrument of claim 1, wherein the forceps cutter for cutting comprises a forceps assembly, including a pair of forceps.

7. The surgical cutting instrument of claim 1 wherein the forceps assembly is welded or threaded to the elongated flexible hollow-body tube.

8. The surgical cutting instrument of claim 1 further containing a control wire displacement device which displaces the control wire for moving the forceps between an open and closed position.

9. A surgical cutting instrument comprising an elongated flexible hollow-body tube having a lumen extending therethrough, and having a proximal and distal end together with an anti-torque outer jacket; a forceps for cutting coupled to the distal end of said hollow body tube; a control wire having proximal and distal ends extending through the lumen and coupled to said forceps; wherein said anti-torque outer jacket comprises wound wire surrounding said flexible tube, and a portion of said wire comprises a right-hand wrap, and another portion comprises a left-hand wrap, and said wire is of uniform diameter and said right-hand and left-hand wraps are attached to one another and are of substantially the same length.

10. The surgical cutting instrument of claim 9 comprising a plurality of said right-hand wraps and left-hand wraps.

* * * * *